(12) United States Patent
Ito et al.

(10) Patent No.: US 11,460,437 B2
(45) Date of Patent: Oct. 4, 2022

(54) ENDOTOXIN DETECTION DEVICE AND ENDOTOXIN DETECTION METHOD

(71) Applicant: TOHOKU UNIVERSITY, Sendai (JP)

(72) Inventors: Takahiro Ito, Sendai (JP); Kumi Inoue, Sendai (JP); Kentaro Ito, Sendai (JP); Hitoshi Shiku, Sendai (JP); Tomokazu Matsue, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 0 days.

(21) Appl. No.: 17/275,013

(22) PCT Filed: Mar. 6, 2020

(86) PCT No.: PCT/JP2020/009859
§ 371 (c)(1),
(2) Date: Mar. 10, 2021

(87) PCT Pub. No.: WO2020/184482
PCT Pub. Date: Sep. 17, 2020

(65) Prior Publication Data
US 2022/0042947 A1 Feb. 10, 2022

(30) Foreign Application Priority Data
Mar. 12, 2019 (JP) .............................. JP2019-045130

(51) Int. Cl.
G01N 33/483 (2006.01)
G01N 27/447 (2006.01)
(Continued)

(52) U.S. Cl.
CPC ......... *G01N 27/44791* (2013.01); *G01N 1/38* (2013.01); *G01N 27/4473* (2013.01);
(Continued)

(58) Field of Classification Search
CPC ............. G01N 33/48721; G01N 14/12; G01N 14/1209; G01N 14/1254; G01N 15/12; G01N 15/1209; G01N 2015/1254
See application file for complete search history.

(56) References Cited

U.S. PATENT DOCUMENTS 2,656,508 A  10/1953  Coulter
4,191,739 A * 3/1980  Uzgiris .................. G01N 15/12
                                                      209/3
(Continued)

FOREIGN PATENT DOCUMENTS

JP  S5480411 A  6/1979
JP  S5942451 A  3/1984
(Continued)

OTHER PUBLICATIONS

Yu et al., Determination of critical micelle concentrations and aggregation numbers by fluorescence correlation spectroscopy: Aggregation of a lipopolysaccharide, Analytica Chimica Acta 556 (2006) 216-225 (Year: 2006).*
Friedrich Birger Anspach, "Endotoxidn removal by affinity sorbents," J. Biochem. Biophys. Methods 49 (2001) 6665-681 (Year: 2001).*
(Continued)

*Primary Examiner* — Alexander S Noguerola
(74) *Attorney, Agent, or Firm* — Kenja IP Law PC

(57) ABSTRACT

Provided are a device and a method for rapidly and simply detecting endotoxin without using an expensive reagent. The endotoxin detection device includes: a region containing an electrolyte solution; a partitioning member that partitions the region into two compartments such that the two compartments are in communication via a nanopore; a first electrode that is disposed in a first compartment; a second electrode that is disposed in a second compartment and is electrically connected to the first electrode; an electrolyte solution flow generating means that causes electrolyte solution in the first
(Continued)

compartment to move to the second compartment via the nanopore; an application means that applies voltage between the first electrode and the second electrode; and a monitoring means that monitors current.

10 Claims, 8 Drawing Sheets

(51) Int. Cl.
  *G01N 1/38* (2006.01)
  *G01N 33/487* (2006.01)
  *G01N 15/12* (2006.01)
(52) U.S. Cl.
  CPC .............. *G01N 33/48721* (2013.01); *G01N 2015/1254* (2013.01)

(56) References Cited

U.S. PATENT DOCUMENTS

| | | | |
|---|---|---|---|
| 4,495,067 A * | 1/1985 | Klein | A61K 9/0019 210/257.2 |
| 2007/0202008 A1* | 8/2007 | Schembri | G01N 33/92 422/400 |
| 2007/0203008 A1* | 8/2007 | Parker | B42C 5/00 493/416 |
| 2010/0122907 A1* | 5/2010 | Stanford | G01N 33/48721 204/451 |
| 2013/0092541 A1 | 4/2013 | Drndic et al. | |
| 2014/0183040 A1* | 7/2014 | Kawai | G01N 27/44752 204/450 |
| 2015/0138552 A1* | 5/2015 | Hirono | G01N 21/82 356/337 |

FOREIGN PATENT DOCUMENTS

| | | | |
|---|---|---|---|
| JP | 2008536124 A | 9/2008 | |
| JP | 2015517671 A | 6/2015 | |
| JP | 2016519773 A | 7/2016 | |
| JP | 2017037043 A | 2/2017 | |
| JP | 2018072181 A | 5/2018 | |
| JP | 2018072331 A | 5/2018 | |
| WO | WO 2014/172574 A1 * | 10/2014 | G01N 27/26 |

OTHER PUBLICATIONS

English language machine translation of the Description section of JP 2018-72181 A obtained from the EPO website Dec. 28, 2021. (Year: 2018).*
Apetrei et al., "A Protein Nanopore-Based Approach for Bacteria Sensing," Nanoscale Research Letters (2016) 11:501 (Year: 2016).*
Rietschel et al., "Bacterial endotoxin: molecular relationships of structure to activity and function," The FASEB Journal vol. 8, Feb. 1994, pp. 217-224 (Year: 1994).*
Su et al., "Methods of Endotoxin Detection,"Journal of Laboratory Automation 2015 vol. 20(4) 354-364 (Year: 2015).*
Maglia et al., "Enhanced translocation of single DNA molecules through α-hemolysin nanopores by manipulation of internal charge," PNAS Dec. 16, 2008 vol. 105, No. 50, pp. 19720-19725 (hereafter "Maglia"). (Year: 2008).*
Piquet et al., "Electroosmosis through α-Hemolysin That Depends on Alkali Cation Type,"J. Phys. Chem. Lett. 2014, 5, 4362-4367 (Year: 2014).*
Kevin Williams, "Endotoxin Test Concerns of Biologies," American Pharmaceutical Review | Endotoxin Supplement 2013 (Year: 2013).*
Aug. 25, 2021, International Preliminary Report on Patentability issued in the International Patent Application No. PCT/JP2020/009859.
Apr. 7, 2020, International Search Report issued in the International Patent Application No. PCT/JP2020/009859.
Kentaro Ito et al., A Nanopore-based Endotoxin Sensor, Bunseki Kagaku, Aug. 5, 2019, pp. 575-580, vol. 68, No. 8.
Nuno C. Santos et al., Evaluation of Lipopolysaccharide Aggregation by Light Scattering Spectroscopy, ChemBioChem, Jan. 3, 2003, pp. 96-100, vol. 4.
Oct. 20, 2020, Decision to Grant a Patent issued by the Japan Patent Office in the corresponding Japanese Patent Application No. 2020-533044.
Sep. 1, 2020, Notification of Reasons for Refusal issued by the Japan Patent Office in the corresponding Japanese Patent Application No. 2020-533044.
Takashi Ito et al., Simultaneous Determination of the Size and Surface Charge of Individual Nanoparticles Using a Carbon Nanotube-Based Coulter Counter, Analytical Chemistry, May 15, 2003, pp. 2399-2406, vol. 75, No. 10.
Apr. 4, 2022, the Extended European Search Report issued by the European Patent Office in the corresponding European Patent Application No. 20770730.8.

* cited by examiner

ENDOTOXIN DETECTION DEVICE AND ENDOTOXIN DETECTION METHOD

TECHNICAL FIELD

The present disclosure relates to an endotoxin detection device and an endotoxin detection method.

BACKGROUND

Examples of conventionally known methods for detecting endotoxin include a detection method (LAL method) that uses a reagent produced from a blood cell extract derived from horseshoe crabs and that is based on the gel forming ability of this reagent with endotoxin from Gram-negative bacteria being dependent on the endotoxin concentration (refer to Patent Literature (PTL) 1) and a method of electrochemically detecting endotoxin that takes the LAL method as a base (refer to PTL 2 and 3).

CITATION LIST

Patent Literature

PTL 1: JP-S59-42451A
PTL 2: JP2018-072331A
PTL 3: JP2017-037043A

SUMMARY

Technical Problem

However, although methods using LAL reagent have high sensitivity, they suffer from problems that LAL reagent is expensive, and that the reaction of LAL required for detection of endotoxin is time consuming. Specifically, the method described in PTL 1 takes roughly 1 hour, whereas the methods described in PTL 2 and 3 require 30 minutes to 1 hour. Therefore, there is demand for a method of rapidly detecting endotoxin without using an expensive reagent.

Accordingly, an object of the present disclosure is to provide a device and method for rapidly and simply detecting endotoxin without using an expensive reagent.

Solution to Problem

The problem described above is solved by a device according to the present disclosure that is set forth below.

An endotoxin detection device comprising:
a region containing an electrolyte solution;
a partitioning member that partitions the region into two compartments such that the two compartments are in communication via a nanopore;
a first electrode that is disposed in a first compartment;
a second electrode that is disposed in a second compartment and is electrically connected to the first electrode;
an electrolyte solution flow generating means that causes electrolyte solution in the first compartment to move to the second compartment via the nanopore;
an application means that applies voltage between the first electrode and the second electrode; and
a monitoring means that monitors current.

Advantageous Effect

According to the present disclosure, it is possible to provide a device and method for rapidly and simply detecting endotoxin without using an expensive reagent as a result of including the configuration set forth above.

BRIEF DESCRIPTION OF THE DRAWINGS

In the accompanying drawings.

DETAILED DESCRIPTION

The following provides a detailed description of an embodiment of the present disclosure (hereinafter, referred to as "the present embodiment"). However, the present disclosure is not limited by the following description and can be implemented with various alterations that are within the scope of the essence of the present disclosure.

[Endotoxin Detection Device]

Figure 1:
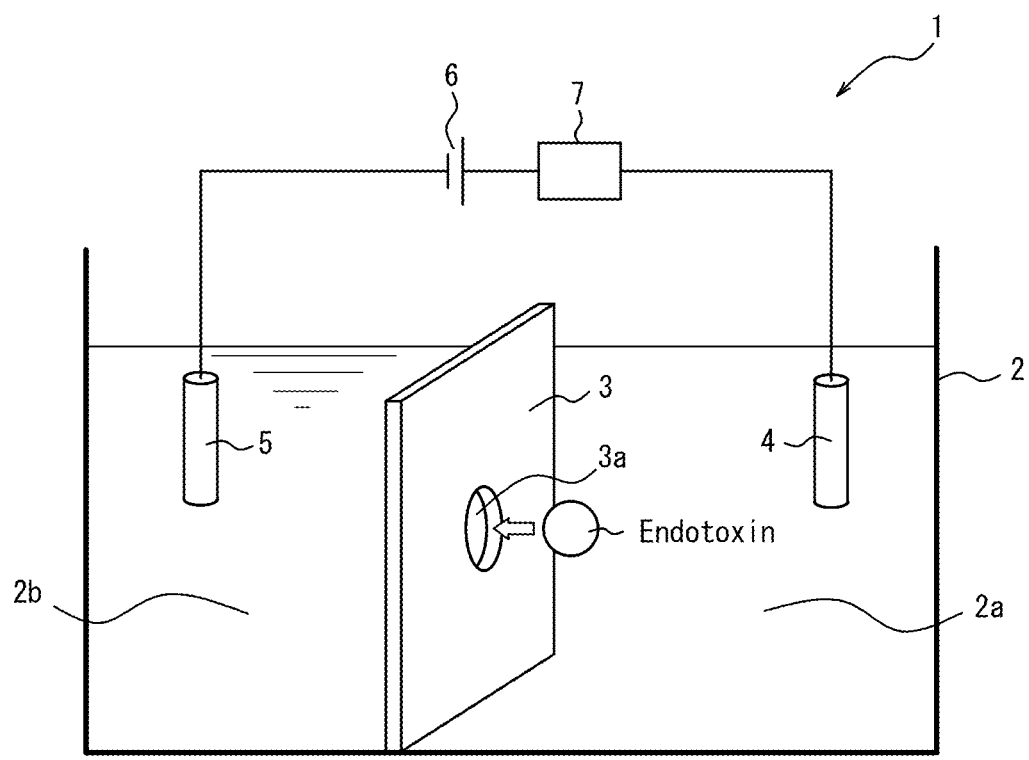
FIG. 1 is a schematic view illustrating an example of an endotoxin detection device according to a present embodiment.
Figure 2:
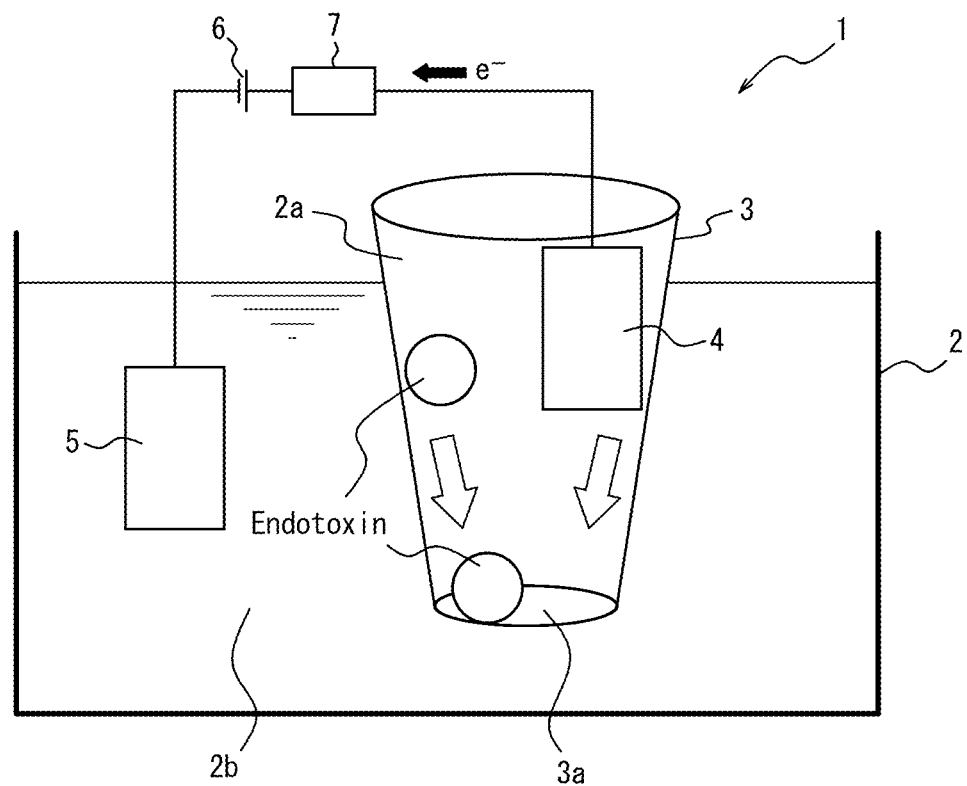
FIG. 2 is a schematic view for description of an endotoxin detection device in Example 1.
Figure 3:
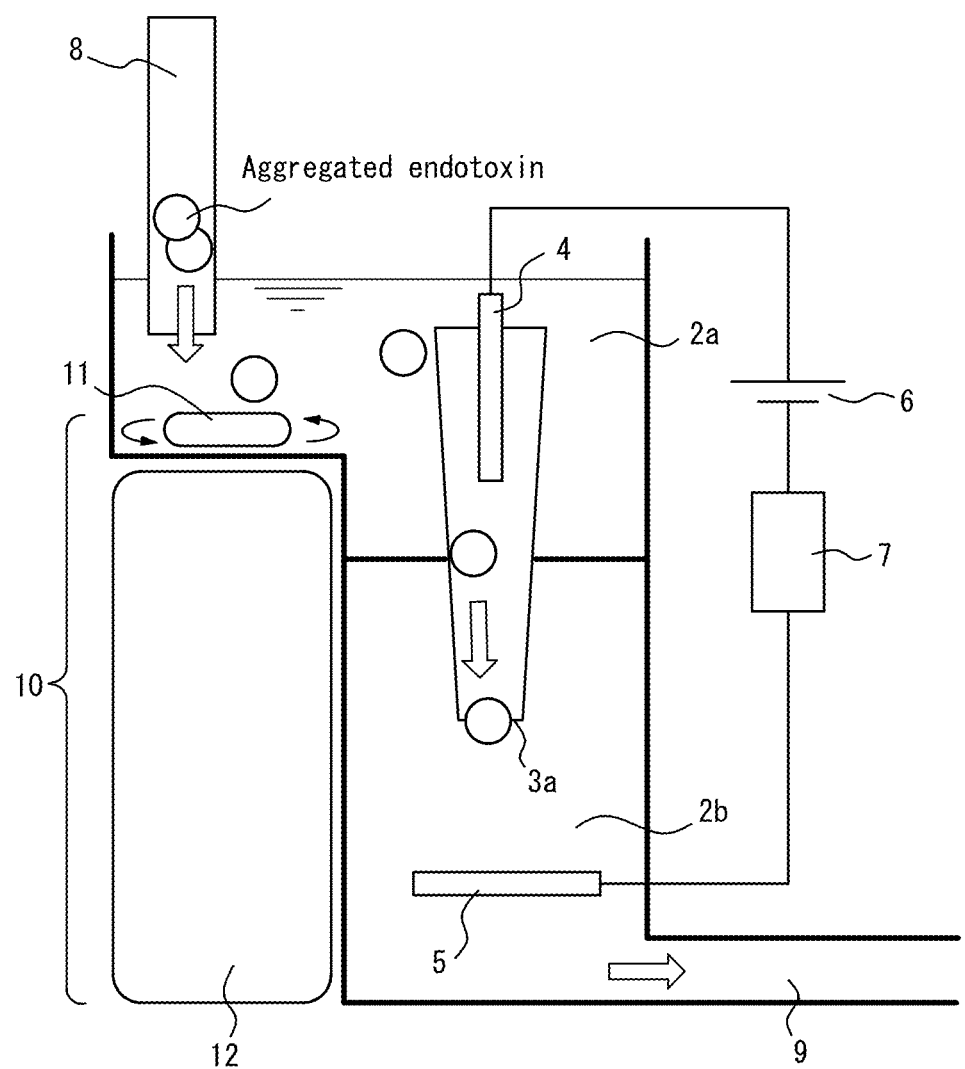
FIG. 3 is a schematic view for description of an example of a continuous measurement system in which an endotoxin detection device according to a present embodiment is used.
Figure 4:
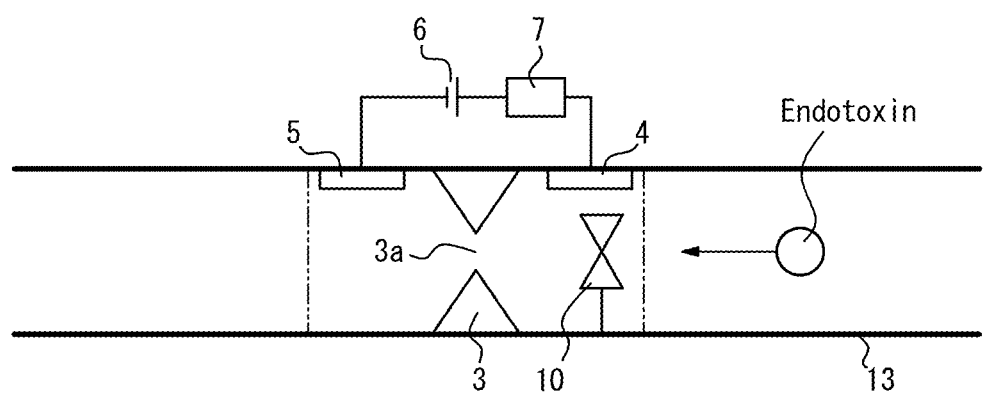
FIG. 4 is a schematic view for description of an example in which an endotoxin detection device according to a present embodiment is adopted in a line for a medical solution.

FIG. 1 illustrates an example of an endotoxin detection device according to the present embodiment. Moreover, FIGS. 2 to 4 illustrate other examples of the endotoxin detection device according to the present embodiment.

An endotoxin detection device 1 incudes: a vessel (region) 2 that contains an electrolyte solution; a partitioning member 3 that partitions the vessel 2 into two compartments (for example, a first compartment 2a and a second compartment 2b) such that the two compartments are in communication via a nanopore 3a; a first electrode 4 that is disposed in the first compartment 2a; a second electrode 5 that is disposed in the second compartment 2b and is electrically connected to the first electrode; an electrolyte solution flow generating means that causes electrolyte solution in the first compartment 2a to move to the second compartment 2b via the nanopore 3a; an application means 6 that applies voltage between the first electrode 4 and the second electrode 5; and a monitoring means 7 that monitors current.

In the endotoxin detection device 1, the electrolyte solution fills at least the entire internal diameter of the nanopore 3a and at least part of each of the first electrode 4 and the second electrode 5 (FIG. 1).

Note that although the endotoxin detection device illustrated in FIG. 1 is an example of a device in which electrolyte solution flows through the nanopore 3a toward the second compartment 2b from the first compartment 2a, the arrangement of the first compartment 2a and the second compartment 2b may be reversed. For example, in FIG. 2, the inside of the vessel 2 may be defined as the first compartment 2a, the inside of a pipette may be defined as the second compartment 2b, and electrolyte solution containing endotoxin may flow in a direction such that it is taken into the pipette.

The endotoxin detection device according to the present embodiment can cause electrolyte solution containing endotoxin in the first compartment 2a to move to the second compartment 2b via the nanopore 3a. It is preferable that the two compartments are only connected via the nanopore 3a (FIGS. 1 and 2).

Note that the nanopore 3a, etc., are enlarged in FIGS. 1 and 2 in order to facilitate understanding.

The following describes the endotoxin detection device in which electrolyte solution flows through the nanopore 3a.

When voltage is applied between the first electrode 4 inside the first compartment 2a and the second electrode 5 inside the second compartment 2b, for example, an ion current flows via the nanopore 3a that connects the two compartments. Here, the first electrode 4 is defined as positive and the second electrode 5 is defined as negative.

Endotoxin tends to form micelles in an aqueous solution. For example, in a situation in which endotoxin is present in electrolyte solution inside the first compartment 2a, the endotoxin forms micelles in the electrolyte solution. When the electrolyte solution flow generating means causes the electrolyte solution to flow toward the second compartment 2b from the first compartment 2a, the endotoxin micelles are carried by the flow of the electrolyte solution and thus flow through the nanopore 3a from the first compartment 2a to the second compartment 2b. When a micelle passes through the nanopore 3a while voltage is being applied, the amount of the electrolyte solution that is passing through the nanopore 3a decreases by an amount equivalent to the volume of the micelle, electric resistance of the nanopore changes, and a pulse current is generated. By measuring changes of the ion current flowing in the nanopore through the monitoring means 7, it is possible to detect endotoxin micelles that have passed through the nanopore 3a. Moreover, the endotoxin concentration of the electrolyte solution in the first compartment 2a can be measured from the frequency of pulse currents or the like.

The electrolyte solution flow generating means may be a means such as a pump that sucks in electrolyte solution, a physical means that injects electrolyte solution, or a means that generates electrophoretic flow or electroosmotic flow through application of voltage between electrodes. By generating electroosmotic flow, it is possible to increase the amount of liquid that passes through the nanopore 3a per time and thus to increase the sensitivity even when the concentration of endotoxin is low. Endotoxins are known to generally have a negative charge. In a case in which the first compartment 2a is formed of glass or the like, an inner wall of the first compartment 2a becomes negatively charged, and an electric double layer forms in proximity to the inner wall.

Improvement of sensitivity is anticipated in this situation because the negatively charged endotoxin is carried by the electroosmotic flow without adhering to the inner wall.

No specific limitations are placed on the vessel 2 so long as it can be partitioned into the first compartment 2a and the second compartment 2b by the partitioning member 3.

The vessel 2 may have an introduction channel by which an electrolyte solution (for example, an electrolyte solution containing endotoxin or a sample that could contain endotoxin) or the like is introduced into the first compartment 2a. Moreover, the second compartment 2b may have a withdrawal channel by which the electrolyte solution is withdrawn. The electrolyte solution is preferably agitated prior to measurement (for example, prior to passing through the nanopore) from a viewpoint of causing endotoxin to be present as individual micelles. The endotoxin detection device preferably includes an agitation means 10 inside the first compartment 2a as illustrated in FIG. 3. The agitation means 10 is preferably included inside the first compartment (for example, between the first electrode and the nanopore) (FIGS. 3 and 4) but may be included in an introduction channel that is in communication with the first compartment.

The vessel 2 may be a hermetically sealed vessel from a viewpoint of preventing contamination with endotoxin from outside of the system and volatilization of the electrolyte solution.

The material of the vessel 2 may, for example, be plastic such as polypropylene, polystyrene, or polyethylene terephthalate, or glass. The material may differ for the first compartment and the second compartment. For example, the first compartment may be a material to which endotoxin does not readily adsorb and the second compartment may be a material to which endotoxin adsorbs from a viewpoint of reducing the endotoxin concentration in electrolyte solution that has been inspected for the presence of endotoxin.

The material to which endotoxin adsorbs may be a positively charged material, a histidine-coated material, a TORAYMYXIN-coated material, a polymyxin B-coated material, a poly(γ-methyl L-glutamate)-coated material, or the like.

The material to which endotoxin does not readily adsorb may be a negatively charged material, borosilicate, or the like.

Of these materials, glass is preferable for forming the first compartment 2a in terms of ease of reliably forming a nanopore having a fine diameter, cost, and the relationship of endotoxin and electroosmotic flow.

The partitioning member 3 may be a wall-shaped member (FIG. 1) or may be a member that forms an independent first compartment 2a inside the vessel 2 (FIG. 2). The member that forms an independent first compartment may, for example, be a capillary, a pipette, a funnel, an injection needle, or the like, and is preferably a capillary or a pipette from viewpoints of inexpensiveness, ease of processing, and the ability to form a nanopore having a fine diameter.

The material forming the partitioning member may, for example, be plastic such as polypropylene, polystyrene, or polyethylene terephthalate, glass, or the like, and is preferably a material to which endotoxin does not readily adsorb, and more preferably glass from a viewpoint of more accurately detecting whether endotoxin is present in a sample.

The surface of the partitioning member at a side where the first compartment 2a is located preferably has a fixed charge from a viewpoint of generating electroosmotic flow in the entire first compartment 2a and efficiently detecting endotoxin.

The term "fixed charge" refers to a charge that is fixed at a surface and does not include charges of components in the electrolyte solution.

The material having a fixed charge may be glass, a material into which a functional group having a fixed charge has been introduced, hexamethyldisilazane, or the like. The fixed charge may be a positive charge or a negative charge. Moreover, surface treatment may be performed so as to provide the fixed charge. For example, treatment may be performed through introduction of a functional group such as a silanol group, a carboxyl group, a sulfo group, an amino group, or a phosphate group, through addition polymerization, or the like, or addition treatment of a fixed charge to the surface may be performed through a modification reaction or the like. Moreover, the surface may be coated with a component having a fixed charge (for example, silicon nitride or the like). Of these examples, glass to which endotoxin does not readily adsorb is preferable.

The shape of the nanopore 3a can be any shape without any specific limitations so long as it is a shape that connects the first compartment 2a and the second compartment 2b and may be a cylindrical shape or the like. The cross-sectional shape of the nanopore 3a may differ or be the same in a length direction of a hole passing through the nanopore 3a.

The internal diameter of the nanopore 3a can be selected as appropriate depending on the objective, but is preferably 2,000 nm to 10 nm, more preferably 800 nm to 50 nm, even more preferably 500 nm to 50 nm, and even more preferably 300 nm to 50 nm. Note that in a case in which the internal diameter of the nanopore differs in the length direction of the hole passing through the nanopore, the minimum internal diameter of the nanopore may be designed so as to be within any of the ranges set forth above.

The nanopore 3a may be formed from the same material as the partitioning member 3, with formation of both the partitioning member 3 and the nanopore from glass being preferable.

Moreover, an inner surface of the nanopore 3a may be subjected to the same treatment as the partitioning member 3.

A preferable example of a partitioning member 3 in which a nanopore having a fine diameter can be formed cheaply and reliably is a glass pipette (produced by Sutter Instruments) having a nanopore at a tip thereof.

The material of the aforementioned electrodes may be a metal such as gold, platinum, titanium, aluminum, tungsten, copper, iron, or palladium; a carbon material such as carbon nanotubes, Ketjenblack, glassy carbon, graphene, fullerene, carbon fiber, carbon fabric, or carbon aerogel; a conductive polymer such as polyaniline, polyacetylene, polypyrrole, poly(p-phenylene vinylene), polythiophene, or poly(p-phenylene sulfide); a semiconductor such as silicon, germanium, indium tin oxide (ITO), titanium oxide, copper oxide, or silver oxide; or the like. Of these materials, a silver-silver chloride electrode is preferable from a viewpoint of stability of electric potential.

The first electrode and the second electrode are electrically connected. This electrical connection may be connection through a conductive member, and no specific limitations are placed on the conductive material that is used.

The application means 6 can, for example, be a device that can continuously apply a certain voltage between the first electrode 4 and the second electrode 5, or the like.

The monitoring means 7 can, for example, be a device that can measure an ion current flowing between the first electrode 4 and the second electrode 5 via the nanopore 3a, or the like. The monitoring means is preferably a device that can detect a pulse current of 30 pA or more, and more preferably a device that can detect a pulse current of 10 pA or more.

The electrolyte solution may be a different electrolyte solution for each of the first compartment and the second compartment but is preferably the same electrolyte solution in terms of composition with the exception of endotoxin concentration. The electrolyte solution may be a solution in which endotoxin can dissolve, for example, and may be phosphate-buffered saline (PBS), an artificial dialysate, an injection liquid, saline, a cleaning liquid for a medical instrument, a feedstock for a pharmaceutical, or the like. Of these examples, an artificial dialysate or injection liquid in which endotoxin readily forms micelles is preferable.

The endotoxin detection device according to the present embodiment may, for example, be a combination of a nano glass pipette that includes a nanopore 3a and has an electrode 4 inserted therein and a vessel (region) that has an electrode 5 inserted therein, such as illustrated in FIG. 2, or may be a microfluidic device or an electrode chip that is surface coated with silicon nitride and includes a compartment having a positive electrode and a compartment having a negative electrode that are connected by a nanopore.

[Continuous Measurement System]

FIG. 3 illustrates a specific example of a continuous measurement system according to the present embodiment. Note that similar elements corresponding to FIGS. 1 and 2 are allocated the same numbers in FIG. 3.

The continuous measurement system includes an introduction channel 8 by which a liquid that is to be measured is introduced. An agitation means 10 that serves as a means for breaking up aggregation of endotoxin micelles is disposed in a section where the introduction channel 8 connects to an endotoxin detection device. Although the agitation means 10 is illustrated as a mechanism in which a magnetic stirrer 12 causes a stirring bar 11 to rotate in FIG. 3, the agitation means 10 is not limited thereto.

A rotor that is rotated by a motor or the like may be used as the agitation means 10, or a known agitation means such as an ultrasonic agitation means can be used as the agitation means 10. Micelles of endotoxin tend to aggregate, but by breaking up this aggregation and then performing measurement, accurate measurement can be performed when endotoxin passes through a nanopore. An agitation means that uses a rotor can directly impart shear stress and can efficiently break up aggregation. Moreover, an agitation means that uses ultrasound or the like is advantageous in a case in which the measured liquid is to be used after measurement because the agitation means does not come into direct contact with the measured liquid.

In FIG. 3, endotoxin micelles are measured using the endotoxin detection device 1 after aggregation thereof has been broken up by the agitation means 10. Liquid for which measurement has been completed is discharged from a withdrawal channel 9 and is then disposed of or is transported to a desired device in accordance with the objective of use.

[Medical Solution Production System]

A medical solution production system according to the present embodiment includes the endotoxin detection device according to the present embodiment set forth above. By incorporating the endotoxin detection device set forth above into a production line for a medical solution and by causing the medical solution to flow into the endotoxin detection device continuously or intermittently in order to inspect the medical solution, endotoxin in the medical solution can be detected.

The medical solution production system may, for example, be a medical solution production system for an artificial dialysate, an injection liquid, saline, a cleaning liquid for a medical instrument, a feedstock for a pharmaceutical, or the like.

In the medical solution production system, a portion of the medical solution may be caused to flow into the endotoxin detection device for inspection, or all of the medical solution may be caused to flow into the endotoxin detection device for inspection. Moreover, since the introduced electrolyte solution is used without being mixed with another reagent in the endotoxin detection device according to the present embodiment, medical solution that has passed through the detection device can be returned to the production line.

The medical solution production system enables simple and efficient inspection for endotoxin because inspection of endotoxin in a medical solution can be performed on the spot as an inline sensor without the need to pretreat the medical solution for inspection, for example. Moreover, the system can be suspended at once upon detection of endotoxin, which enables reduction of production cost of the medical solution.

The following describes a specific example in which the medical solution production system is adopted.

FIG. 4 illustrates an example in which the present disclosure is adopted in a line for a medical solution, and, in particular, for an artificial dialysate. Note that similar elements corresponding to FIGS. 1, 2, and 3 are allocated the same numbers in FIG. 4.

An endotoxin detection device 1 includes a partitioning member 3 that partitions an artificial dialysate line 13 into two compartments (2a and 2b) such that the compartments are in communication via a nanopore 3a, a first electrode 4 disposed in a first compartment, a second electrode 5 disposed in a second compartment, and an agitation means 10 disposed at an upstream side.

The endotoxin detection device 1 can be configured as an adapter-type device in which at least the partitioning member 3, the first electrode 4, and the second electrode 5 are integrated and that can be installed in the line so as to be cheap and easily maintainable through replacement at a certain timing, for example. In a case in which an agitation means such as a rotor is used, the agitation means may also be incorporated into the adapter.

In a case in which the endotoxin detection device is incorporated into an artificial dialysate line, the device may be incorporated directly into the artificial dialysate line in order to inspect all of the artificial dialysate, or a branch pipe may be provided in the line so as to extract and measure only a portion of the dialysate. Dialysate that has been measured in the branch pipe may be returned to the line or may be disposed of.

The use of a branch pipe enables efficient measurement of dialysate.

[Endotoxin Detection Method]

In an endotoxin detection method according to the present embodiment, the endotoxin detection device according to the present embodiment set forth above is used to detect endotoxin by measuring changes of an ion current value through the monitoring means 7.

When an endotoxin micelle passes through the nanopore, the ion current value changes (FIGS. 6A to 6D and FIG. 8) relative to an ion current (background ion current) generated when electrolyte solution that does not contain endotoxin flows. Changes of the ion current value mainly appear as pulse currents. The size of an endotoxin micelle can be determined from the size of a pulse current. Moreover, the concentration of endotoxin micelles can be determined from the frequency of pulse currents.

Note that a base value of the ion current can be adjusted through the type of electrolyte solution, the internal diameter of the nanopore, or the like, for example.

Figure 8:
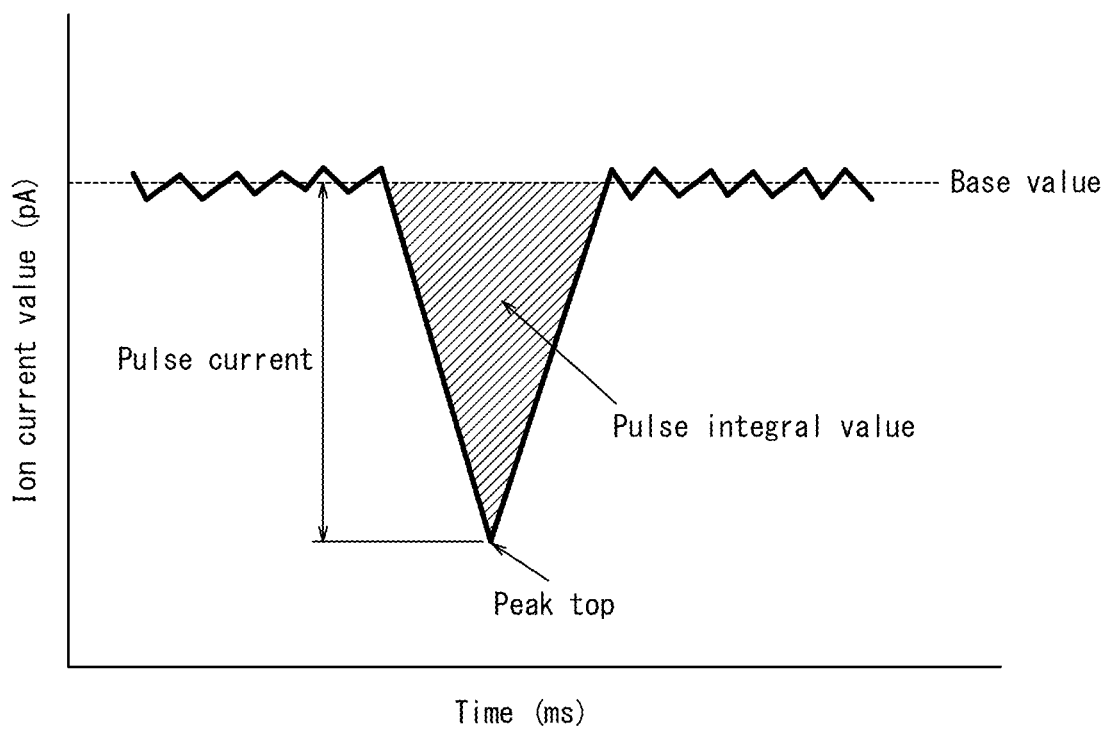
FIG. 8 is a diagram for description of a pulse current and a pulse integral value.

The pulse current referred to above is taken to be a pulse current for which, in a graph of time (ms) on a horizontal axis and ion current value (pA) on a vertical axis, there is a significant difference between a peak top of the pulse current value and a base value, which is taken to be the average of the ion current value for 50 ms before and after the pulse (100 ms in total) (FIG. 8). The pulse current for which there is a significant difference is preferably a pulse current value that has changed by 1.5 times or more, more preferably 1.8 times or more, and even more preferably 2 times or more relative to the difference between an upper limit and a lower limit of the base value. Such a pulse current is judged to be due to a micelle passing through the nanopore. The specific pulse current value is preferably 30 pA or more, and more preferably 50 pA or more.

Figure 6A:
FIG. 6A illustrates an example of pulse currents measured using an electrolyte solution having an endotoxin concentration of 500 EU/L in Example 1.
Figure 6B:
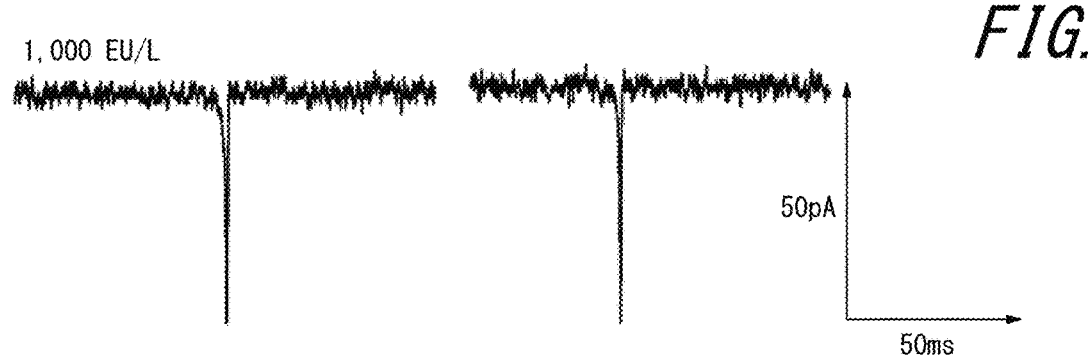
FIG. 6B illustrates an example of pulse currents measured using an electrolyte solution having an endotoxin concentration of 1,000 EU/L in Example 1.
Figure 6C:
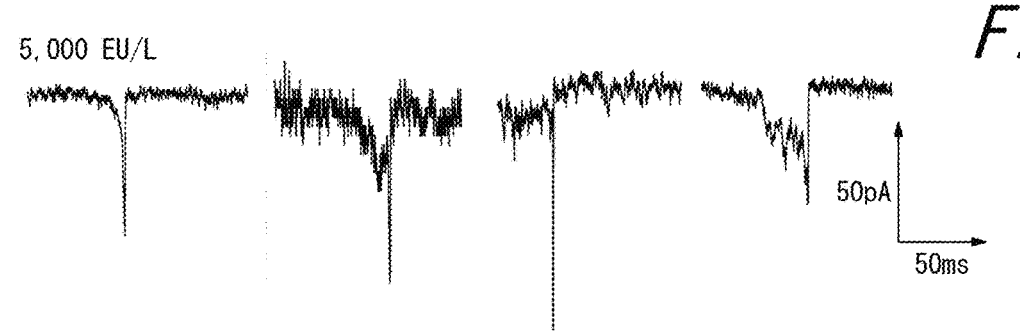
FIG. 6C illustrates an example of pulse currents measured using an electrolyte solution having an endotoxin concentration of 5,000 EU/L in Example 1.
Figure 6D:
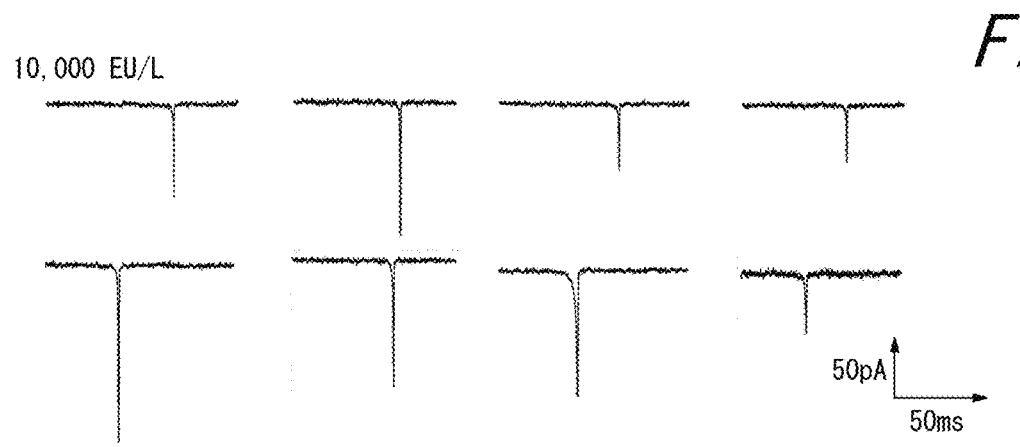
FIG. 6D illustrates an example of pulse currents measured using an electrolyte solution having an endotoxin concentration of 10,000 EU/L in Example 1.

Note that there are instances in which a pulse current is generated continuously or is generated in a spread out manner in the time axis direction for some reason or other as illustrated by the drawing furthest to the right in FIG. 6C. When peak tops of a preceding pulse current and a subsequent pulse current are not separated by an interval of 50 ms in such a situation, these pulse currents are considered to be a single pulse current.

Moreover, in a case in which the volume of an endotoxin micelle is to be estimated for each pulse in a graph of time (ms) on a horizontal axis and ion current value (pA) on a vertical axis, the volume of the endotoxin micelle can be estimated from the area surrounded by the base value and the pulse waveform (hatched section in FIG. 8; referred to as a "pulse integral value" in the present specification).

The pulse current preferably has a pulse integral value of 200 pA·ms or more, more preferably 300 pA·ms or more, and even more preferably 400 pA·ms or more. By measuring both the frequency of pulses and pulse integral values, the endotoxin concentration can be more accurately measured.

The flow rate of electrolyte solution in the nanopore can be any flow rate so long as endotoxin can be detected and is preferably 5 µL/min to 0.1 µL/min, more preferably 1 µL/min to 0.1 µL/min, and even more preferably 0.6 µL/min to 0.1 µL/min.

The voltage applied between the first electrode 4 and the second electrode 5 is preferably 3.0 V to 0.1 V with which an ion current that enables simple detection of endotoxin is obtained, and is more preferably 2.0 V to 0.5 V, and even more preferably 1.0 V to 0.5 V.

No specific limitations are placed on the detection time, and detection may be performed within 4 minutes or may be performed continuously. For example, detection may be stopped at a point at which the presence of endotoxin is detected.

An electrolyte solution that contains endotoxin is preferably agitated and mixed in advance in order to enable more accurate measurement of concentration by homogenizing the size of endotoxin micelles. The agitation and mixing are preferably performed by mixing at 2,000 rpm to 3,000 rpm for 20 minutes to 40 minutes.

Endotoxin detection may be performed while introducing an electrolyte solution into the first compartment 2a and discharging the electrolyte solution from the second compartment 2b.

Through the endotoxin detection method according to the present embodiment, by measuring the pulse frequency (frequency of changes of an ion current value) for reference electrolyte solutions having known endotoxin concentrations, preparing a calibration curve with pulse frequency on a vertical axis and endotoxin concentration on a horizontal axis (FIG. 7), for example, and comparing the calibration curve to the pulse frequency for a sample having an unknown endotoxin concentration, it is possible to measure the endotoxin concentration of the sample.

EXAMPLES

The following provides a more specific description of the present disclosure based on examples. However, the present disclosure is not limited by these examples.

(Used Reagents, Materials, Etc.)
Standard endotoxin: USP-RSE produced by Seikagaku Corporation
Phosphate-buffered saline (PBS): Prepared by dissolving Dulbecco's phosphate-buffered saline powder (FUJIFILM Wako Pure Chemical Corporation) in water for injection (Otsuka Pharmaceutical Co., Ltd.)
Endotoxin solutions: Prepared by dissolving standard endotoxin in water for injection (Otsuka Pharmaceutical Co., Ltd.) (note that endotoxin solution preparation was performed at a clean bench to prevent inclusion of endotoxin from the atmosphere)
Ag/AgCl wire: Produced through electrolytic deposition of AgCl in 0.1 M HCl with respect to Ag wire (99.99%; produced by Tanaka Kikinzoku Kogyo) of 0.3 mm in diameter (Nanopipette Production)
Glass nanopipettes were each produced by pulling a borosilicate tube (external diameter: 1.0 mm; internal diameter: 0.5 mm; BF100-50-7.5) produced by Sutter Instrument using a $CO_2$ laser puller (Model P-2000) produced by Sutter Instrument. The program parameters of the laser puller were set as: heat=300, filament=3, velocity=30, delay=150, pull=50.

The tip diameters of produced glass nanopipettes were evaluated using a scanning electron microscope (SEM; JSM-7100F produced by JEOL Ltd.).

Figure 5A:
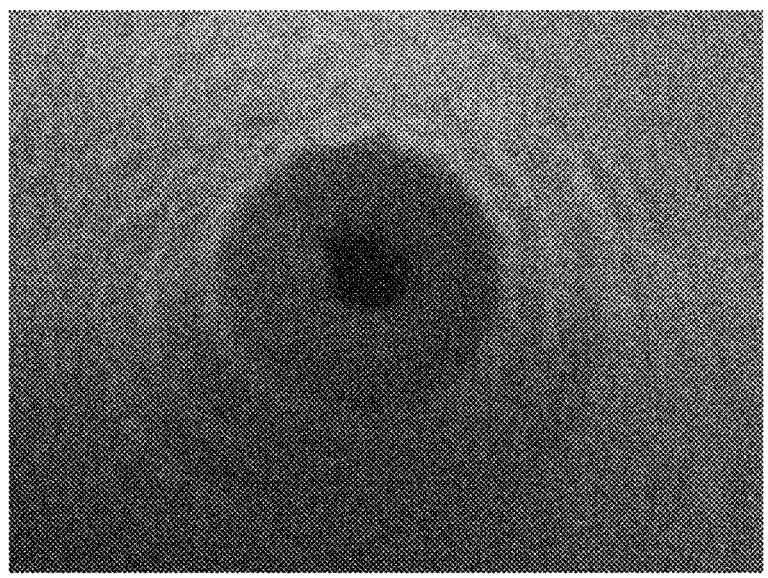
FIG. 5A is an SEM image of a tip of a nanopipette produced in Example 1.

An SEM image of a nanopipette tip is illustrated in FIG. 5A. When the pore diameters of 6 glass pipettes were measured by the SEM, the average was 260 nm, and the standard deviation was 18 nm. It was confirmed that nanopipettes having little variation of nanopore diameter were obtained.

In addition, the inside of a glass nanopipette was filled with endotoxin-free PBS, Ag/AgCl wires were inserted inside and outside of the glass nanopipette, a voltage of 1 V was applied, and background current was measured. Ion current measurement and voltage control were performed using a patch-clamp amplifier (MultiClamp 700B) produced by Axon Instruments.

Figure 5B:
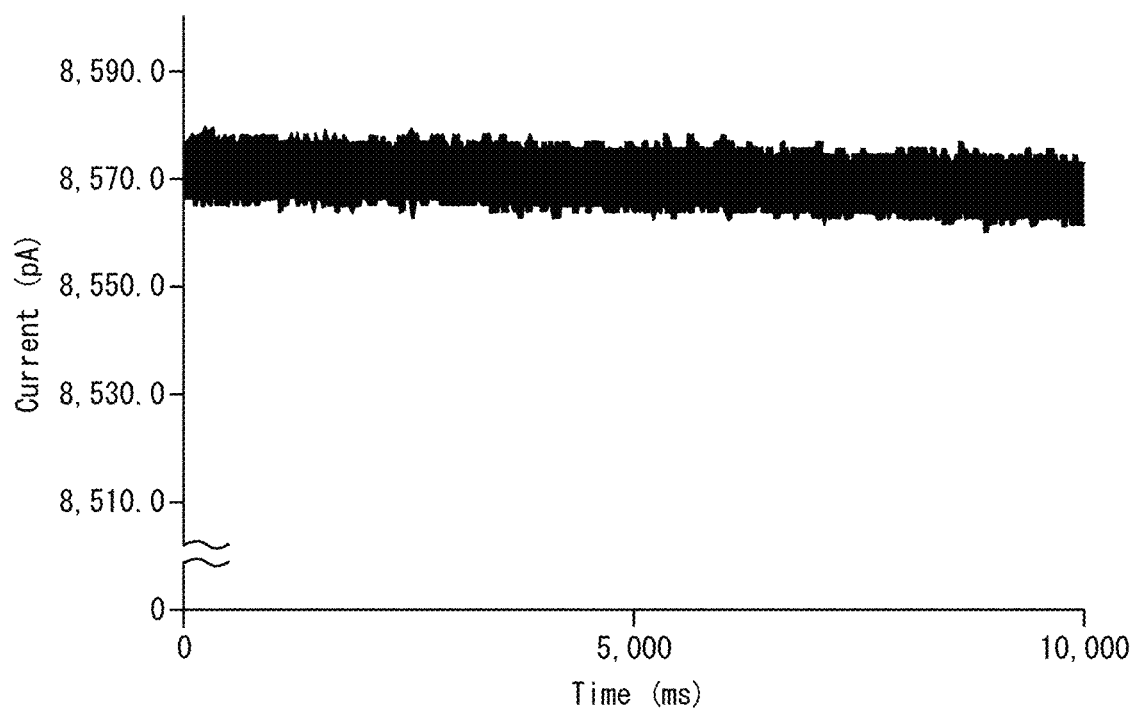
FIG. 5B illustrates results of measurement of background current using glass pipettes produced in Example 1.

A constant current of 8.570±0.009 nA flowed with the first glass nanopipette, and upon measurement using three glass pipettes, the average was 8.572 nA and the standard deviation was 6.228 pA (FIG. 5B).

These results indicate that a pulse current is not observed for endotoxin-free PBS.

Upon measurement of the flow rate of electroosmotic flow, the flow rate was determined to be 0.5 μL/min.

Example 1

A vessel (second compartment) made from polystyrene was charged with 2 mL of endotoxin-free PBS, and the tip of a glass nanopipette (first compartment) filled with an endotoxin solution was immersed in the PBS inside the vessel (FIG. 2).

Solutions having endotoxin concentrations of 0 EU/L, 100 EU/L, 500 EU/L, 1,000 EU/L, 5,000 EU/L, and 10,000 EU/L, respectively, were each used as an endotoxin solution with which a pipette was filled. Moreover, a new glass nanopipette was used for each measurement in consideration of endotoxin contamination of the nanopipette inner wall surface. Measurement was repeated three times for each of the concentrations. Note that a glass pipette produced as described above was used as the glass nanopipette.

Ag/AgCl wires were inserted both inside of the glass nanopipette and in the vessel, and a voltage was applied such that the Ag/AgCl wire inside the nanopipette was +1 V relative to the Ag/AgCl wire in the vessel. An ion current value was measured for 4 minutes from when the tip of the nanopipette was immersed in the PBS inside the vessel. Ion current measurement and voltage control were performed using a patch-clamp amplifier (MultiClamp 700B) produced by Axon Instruments.

Upon measurement of the flow rate of electroosmotic flow, the flow rate was determined to be 0.5 μL/min.

RESULTS

The background ion current obtained by causing the electrolyte solution having an endotoxin concentration of 0 EU/L to flow for 4 minutes was 8 nA.

Pulses of 50 pA or more appeared for the endotoxin solutions having an endotoxin concentration of 500 EU/L or more, but did not appear for the endotoxin solutions having endotoxin concentrations of 0 EU/L and 100 EU/L. It may be the case that at a concentration of 100 EU/L or less, the concentration of micelles in the endotoxin solution was low, and micelles of sufficient size for influencing electric resistance of the nanopore could not be formed. Measurement may become possible by, for example, altering the amount of charge inside the nanopore, the type of electrolyte solution, the voltage, the nanopore diameter, the flow rate, and so forth, or by altering the measurement time.

Some of the pulse shapes observed for the various endotoxin concentrations are illustrated in FIGS. 6A to 6D.

The size of peak current values for the various concentrations was approximately 50 pA for 500 EU/L to 1,000 EU/L, approximately 50 pA to 100 pA for 5,000 EU/L, and approximately 50 pA to 200 pA for 10,000 EU/L. An ion current is impaired to a greater degree when a larger micelle passes through a nanopore, and thus it can be seen that larger micelles were present at higher endotoxin concentrations based on the appearance of larger pulse currents.

When the size of a peak relative to fluctuations of the base value before and after the peak was measured for every pulse current value of 20 pA or more observed at 500 EU/L, all of the pulse currents were 2 times or more. Moreover, when a pulse integral value was measured for each pulse current of 20 pA or more, all of the pulse currents had a pulse integral value of 400 pA·ms or more.

When the size of a peak relative to fluctuations of the base value before and after the peak was measured for every pulse current value of 20 pA or more observed at 1,000 EU/L, all of the pulse currents were 2 times or more. Moreover, when a pulse integral value was measured for each pulse current of 20 pA or more, all of the pulse currents had a pulse integral value of 300 pA·ms or more.

When the size of a peak relative to fluctuations of the base value before and after the peak was measured for every pulse current value of 20 pA or more observed at 5,000 EU/L, all of the pulse currents were 2 times or more. Moreover, when a pulse integral value was measured for each pulse current of 50 pA or more, all of the pulse currents had a pulse integral value of 400 pA·ms or more.

When the size of a peak relative to fluctuations of the base value before and after the peak was measured for every pulse current value of 50 pA or more observed at 10,000 EU/L, all of the pulse currents were 2 times or more. Moreover, when a pulse integral value was measured for each pulse current of 50 pA or more, all of the pulse currents had a pulse integral value of 400 pA·ms or more.

Figure 7:
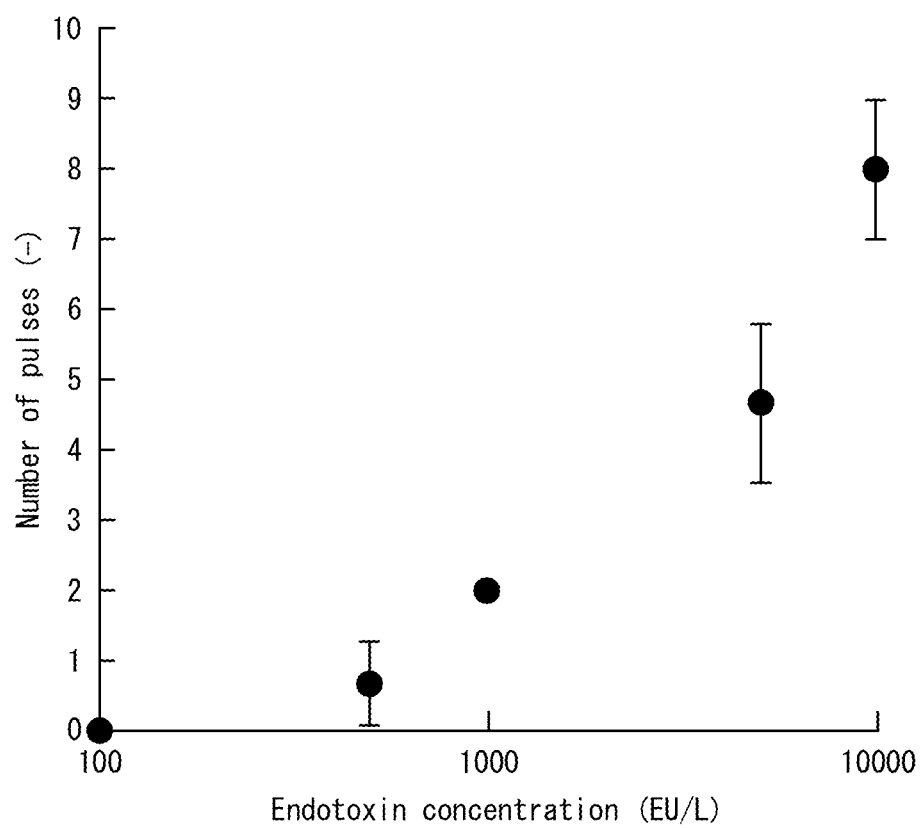
FIG. 7 illustrates a plot of the number of pulses of 30 pA or more measured for solutions having endotoxin concentrations of 100 EU/L, 500 EU/L, 1,000 EU/L, 5,000 EU/L, and 10,000 EU/L, respectively, in Example 1.

FIG. 7 illustrates a calibration curve of the number of pulses of 50 pA or more appearing during 4 minutes of ion current measurement relative to the endotoxin concentration. Each error bar represents the standard deviation (N=3). The frequency with which pulses appeared increased with increasing endotoxin concentration in a range of 500 EU/L to 10,000 EU/L. This indicates that the number of endotoxin micelles that pass through a nanopore per unit time increases with increasing endotoxin concentration. Assuming that 1 micelle passes through a nanopore per 1 pulse, the amount of endotoxin contained per 1 micelle can be calculated to be 0.15 pg at 500 EU/L, 0.13 pg at 1,000 EU/L, 0.21 pg at 5,000 EU/L, and 0.25 pg at 10,000 EU/L. Accordingly, the amount of endotoxin contained per 1 micelle increases with increasing endotoxin concentration, and thus the endotoxin concentration and the number of micelles can be said to have a plateauing non-linear relationship rather than a proportional relationship. It is possible to measure whether or not an unknown sample contains endotoxin and the endotoxin concentration thereof through comparison with the calibration curve obtained in FIG. 7.

Note that the limit of detection in the present example was taken to be the endotoxin concentration at which at least one pulse appeared, which was calculated to be 500 EU/L.

INDUSTRIAL APPLICABILITY

Through the endotoxin detection device and the endotoxin detection method according to the present disclosure, it is possible to rapidly detect endotoxin without using an expensive reagent. Moreover, incorporation into a line for a dialysate, an injection liquid, or the like is possible because endotoxin detection can be performed directly in a flow system without causing a reaction with another reagent.

REFERENCE SIGNS LIST

1 endotoxin detection device
2 vessel (region)
2a first compartment
2b second compartment
3 partitioning member
3a nanopore
4 first electrode
5 second electrode
6 application means
7 monitoring means
8 introduction channel
9 withdrawal channel
10 agitation means
11 stirring bar
12 magnetic stirrer
13 line

The invention claimed is:

1. A medical solution production system for detecting endotoxin in an electrolyte solution, the system comprising an endotoxin detection device that does not use Limulus Amebocyte Lysate reagent, wherein
the endotoxin detection device is incorporated into an artificial dialysate line and comprises:
a region containing the electrolyte solution in the artificial dialysate line;
a partitioning member that partitions the region into two compartments such that the two compartments are in communication via a nanopore;
a first electrode that is disposed in a first compartment;
a second electrode that is disposed in a second compartment and is electrically connected to the first electrode;
an electrolyte solution flow generating device configured to cause the electrolyte solution in the first compartment to move to the second compartment via the nanopore;
an application device configured to apply voltage between the first electrode and the second electrode; and
a monitoring device configured to monitor ion current flowing in the nanopore, and wherein
the electrolyte solution is an artificial dialysate flowing in the artificial dialysate line.

2. The medical solution production system according to claim 1, wherein the endotoxin detection device further comprises an agitation means in proximity to the first compartment.

3. The medical solution production system according to claim 1, wherein the electrolyte solution flow generating device is a device of generating electroosmotic flow.

4. The medical solution production system according to claim 1, wherein a fixed charge is present inside of the nanopore.

5. The medical solution production system device according to claim 1, wherein endotoxin is detected by measuring changes of the ion current value by the monitoring device.

6. The medical solution production system according to claim 1, wherein the endotoxin detection device is an adapter-type device that can be installed in the line.

7. A method for producing a medical solution by using a medical solution production system comprising an endotoxin detection device incorporated into an artificial dialysate line, wherein
the endotoxin detection device does not use Limulus Amebocyte Lysate reagent and comprises:
a region containing the electrolyte solution in the artificial dialysate line;
a partitioning member that partitions the region into two compartments such that the two compartments are in communication via a nanopore;
a first electrode that is disposed in a first compartment;
a second electrode that is disposed in a second compartment and is electrically connected to the first electrode;
an electrolyte solution flow generating device configured to cause the electrolyte solution in the first compartment to move to the second compartment via the nanopore;

an application device configured to apply voltage between the first electrode and the second electrode; and a monitoring device configured to monitor ion current flowing in the nanopore, the electrolyte solution is an artificial dialysate flowing in the artificial dialysate line, and using the endotoxin detection device to detect an endotoxin in the flowing electrolyte solution.

8. The method according to claim 7, wherein endotoxin is detected by measuring changes of the ion current value by the monitoring device.

9. The method according to claim 7, wherein the electrolyte solution is subjected to agitation.

10. The method according to claim 7, wherein reference electrolyte solutions having known endotoxin concentrations are prepared, frequency of changes of an ion current value as endotoxin micelles pass through the nanopore is measured, a calibration curve of the frequency of changes and endotoxin concentration is prepared, and frequency of changes of the ion current for the electrolyte solution having an unknown endotoxin concentration is compared with the calibration curve in order to measure the endotoxin concentration in the electrolyte solution.

* * * * *